United States Patent [19]
Takeuchi et al.

[11] Patent Number: 4,922,906
[45] Date of Patent: May 8, 1990

[54] SMALL-SIZED LOW FREQUENCY CURING APPARATUS

[75] Inventors: Mitsunori Takeuchi, Sagamihara; Minoru Sasaki, Yokohama, both of Japan

[73] Assignee: Kabushiki Kaisya Advance, Tokyo, Japan

[21] Appl. No.: 258,104

[22] PCT Filed: Dec. 4, 1986

[86] PCT No.: PCT/JP86/00615
§ 371 Date: Jul. 31, 1987
§ 102(e) Date: Jul. 31, 1987

[87] PCT Pub. No.: WO87/03497
PCT Pub. Date: Jun. 18, 1987

Related U.S. Application Data

[63] Continuation of Ser. No. 90,247, filed as PCT JP86/00615 on Dec. 4, 1986, published as WO87/03497 on Jun. 18, 1987, abandoned.

[30] Foreign Application Priority Data

Dec. 4, 1985 [JP] Japan .................. 60-271589
Nov. 11, 1986 [JP] Japan .................. 61-266690

[51] Int. Cl.$^5$ .............................................. A61N 1/00
[52] U.S. Cl. ................................. 128/419 R; 128/421; 128/422; 128/783; 128/798; 128/802
[58] Field of Search ............... 128/419 R, 421, 422, 128/783, 798, 799, 802, 803

[56] References Cited
U.S. PATENT DOCUMENTS

| 3,258,013 | 6/1966 | Druz | 128/419 D |
| 3,295,528 | 1/1967 | Masaki | 128/422 |
| 4,018,218 | 4/1977 | Carlson et al. | 128/422 |
| 4,210,150 | 7/1980 | James | 128/421 |
| 4,230,121 | 10/1980 | Stanton | 128/422 |
| 4,582,049 | 4/1986 | Ylvisaker | 128/421 |
| 4,687,004 | 8/1987 | Zenkich | 128/419 R |
| 4,769,881 | 9/1988 | Pedigo et al. | 128/419 R |

FOREIGN PATENT DOCUMENTS

| 0138347 | 4/1985 | European Pat. Off. | 128/422 |
| 2143131A | 2/1985 | United Kingdom | 128/422 |

Primary Examiner—Francis Jaworski
Assistant Examiner—George Manuel
Attorney, Agent, or Firm—Finnegan, Henderson, Farabow, Garrett, Dunner

[57] ABSTRACT

A small-sized low frequency curing apparatus which can be applied directly to the object to be stimulated such as a body or the like.

Generating high frequency boosted pulses by electrical energy from a small-sized power source, accumulating the boosted pulses temporarily until a predetermined amount at which stimulation is effective for the organism is reached, and then discharging the accumulated charges to generate low frequency pulses having an effective amplitude for the stimulation as an electrical stimulation. Thus, it is possible to apply a sufficient magnitude of and a stable electrical stimulation to an object to be stimulated regardless of the small capacity of the small-sized power source.

17 Claims, 16 Drawing Sheets

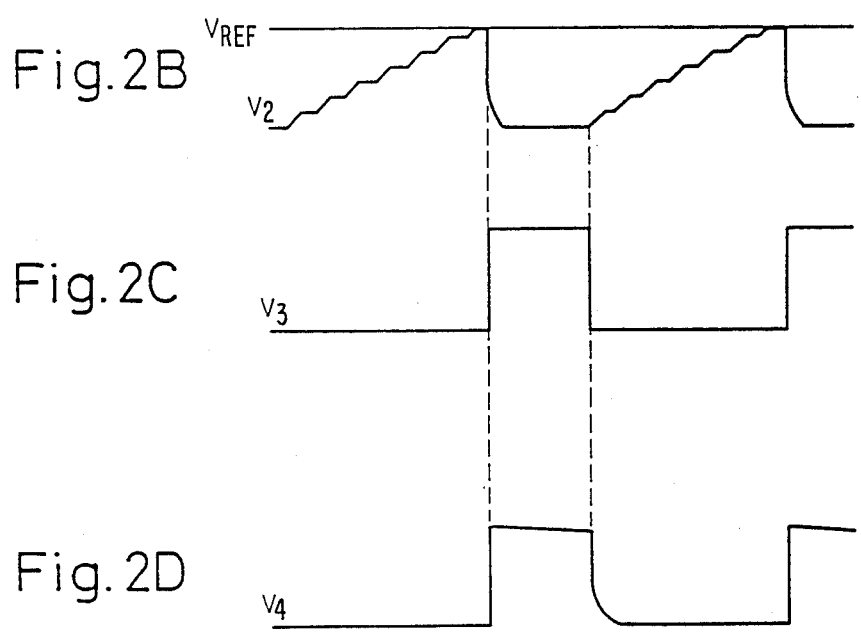

Fig. 4
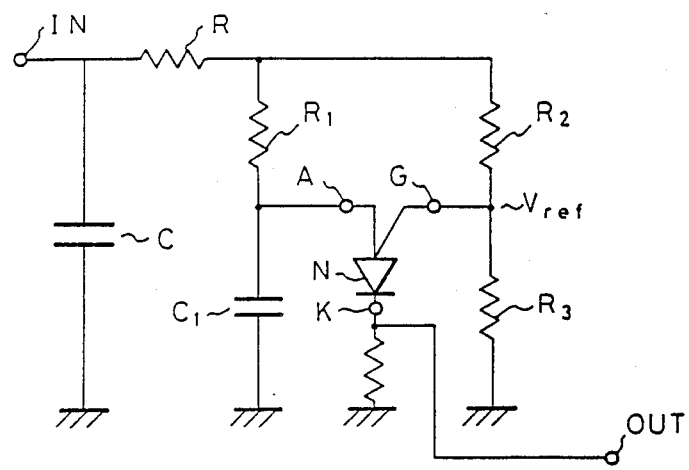
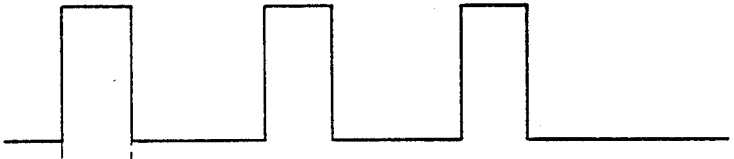
Fig.5A
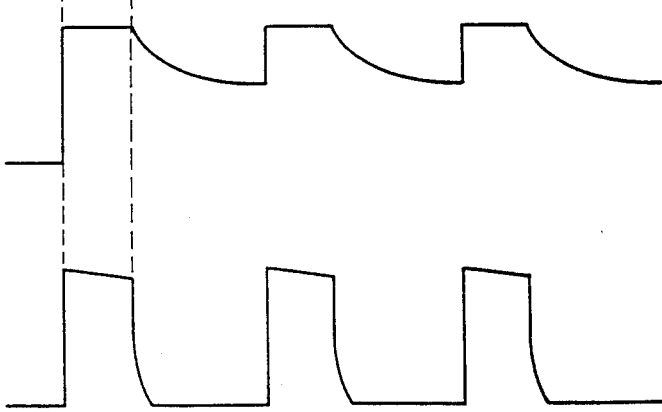
Fig.5B
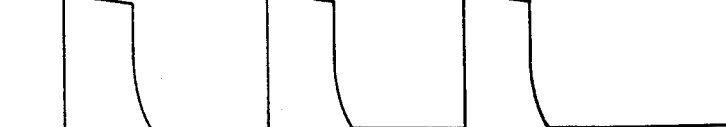
Fig.5C

SMALL-SIZED LOW FREQUENCY CURING APPARATUS

This application is a continuation of application Ser. No. 07/090,247, filed as PCT JP86/00615 on Dec. 4, 1986, published as WO87/03497 on Jun. 18, 1987, now abandoned.

DESCRIPTION

1. Technical Field

The present invention relates to a small-sized low frequency curing apparatus capable of providing an electrical stimulation subject such as an organism with a required electrical stimulation regardless of a small capacity of a power supply and, in particular, to a small-sized low frequency curing apparatus which can be applied directly to the organism and can be produced in a smallest possible size.

2. Background Art

Conventionally, there has been provided and employed an endermic electrical stimulation apparatus, i.e., a so-called low frequency curing apparatus, which has a size such that it is portable and can be applied. However, an apparatus which has a light weight and a size such that it requires no lead line and can be applied to the skin like a bandage, a poultice and the like has not yet been provided. To provide an apparatus which has a light weight and a size such that it can be applied to the skin, as a power supply thereof, a micro battery or small-sized battery such as a button battery, a paper battery and the like must be used. When a small-sized power supply is used, however, the following problems inevitably arise. That is, a skin impedance represents a high resistance value, due to the tissue structure, and accordingly, the application of low frequency high voltage is necessary to supply a cenesthesic low frequency stimulation current, and a boosting means is necessary to generate a high voltage from a low power supply voltage. Cenesthesic electrical stimulation requires a predetermined voltage value and current value. In a small-sized power supply such as a small-sized battery, however, the internal impedance is increased as the discharge current is increased. Accordingly, it is difficult to realize the above conditions.

It has been considered that the above problems can be solved by employing a method including the steps of accumulating battery energy to an extent such that stimulation can be applied to the organism, and discharging this accumulated energy. To effect the setting of the timing of the charge and discharge, or the operation thereof, several active elements are needed, but in many cases, to actually operate such active elements, a supply of a stable required electrical energy is necessary. Therefore, it is almost impossible to meet these conditions by employing the energy of a small-sized battery or a boosted energy obtained by boosting said energy, in the light of the duration time of the battery energy and the battery capacity. Still further, under the conditions of an unstable voltage, a drawback arises in that excessive energy is discharged and dissipated. Accordingly, a practical low frequency curing apparatus using a small-sized battery has not yet been provided.

DISCLOSURE OF THE INVENTION

An object of the present invention is to provide a small-sized low frequency curing apparatus capable of applying cenesthesic electrical stimulation to an organism even though it is constituted from a small number of elements.

Another object of the present invention is to provide a small-sized low frequency curing apparatus capable of supplying long-time and stable electrical stimulation irrespective of the amount of energy of a small-sized power supply.

The above-mentioned objects can be attained by providing a small-sized low frequency curing apparatus comprising: a small-sized power source; boosted pulse generating means for generating a train of boosted pulses upon a receipt of electrical energy from the small-sized power source; accumulating means constituted to receive a train of pulses from the boosted pulse generating means and accumulate electrical energy at least to a predetermined amount at which stimulation effective for an object to be electrically stimulated is reached; and a low frequency pulse outputting means for outputting low frequency pulses when the predetermined amount of electrical energy accumulated in the accumulating means reaches a level at which stimulation is possible for the object to be stimulated.

BRIEF DESCRIPTION OF THE DRAWINGS

FIGS. 2A to 2D are diagrams showing the signal waveform of each point in the apparatus shown in FIG. 1;

FIG. 4 is a circuit diagram showing an example of the construction of the accumulating means and low frequency pulse outputting means shown in FIG. 1;

FIGS. 5A to 5C are diagrams showing the low frequency current waveform for explaining the operation of the de-polarization means shown in FIG. 1;

BEST MODE FOR CARRYING OUT THE INVENTION

Figure 1:
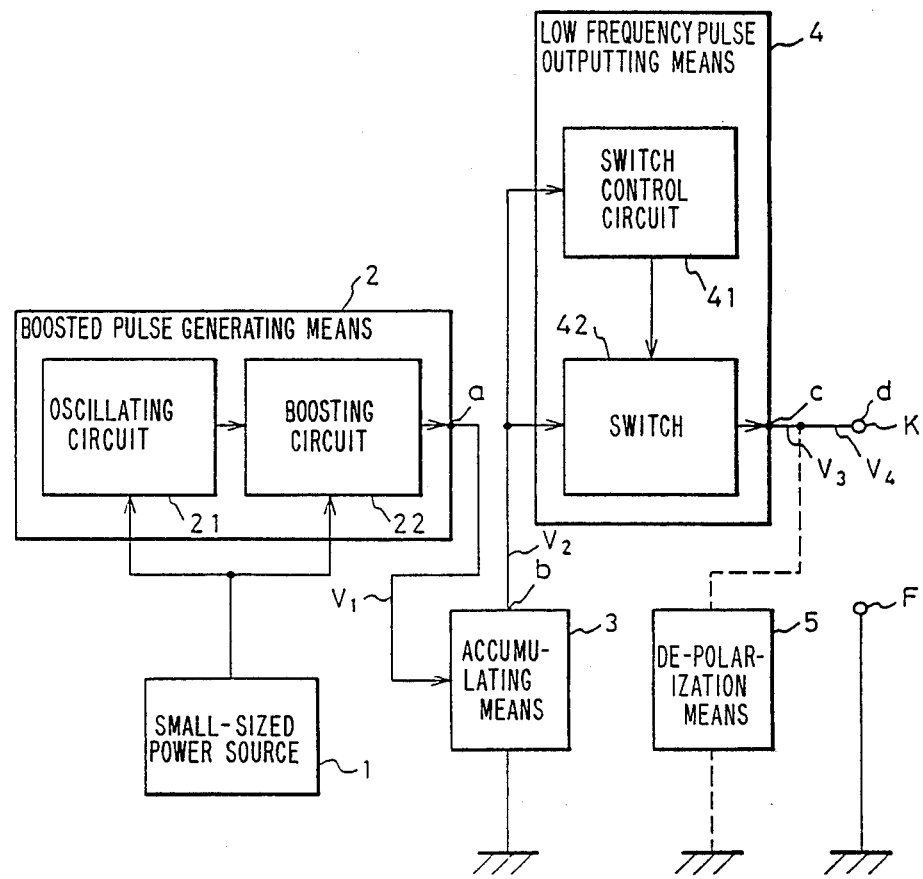
FIG. 1 is a block diagram showing a fundamental constitution of the small-sized low frequency curing apparatus according to the present invention.

FIG. 1 is a block diagram showing a fundamental constitution of the small-sized low frequency curing apparatus according to the present invention, and FIGS. 2A to 2D show the signal waveform of each point in the apparatus shown in FIG. 1.

As shown in FIG. 1, the low frequency curing apparatus of the present invention is constituted by a small-sized power supply 1, a boosted pulse generating means 2 constituted by an oscillating circuit 21 and a boosting circuit 22, an accumulating means 3, a low frequency pulse outputting means 4 constituted by a switch control circuit 41 and a switch 42, and preferably, a de-polarization means 5. K and F denote an electrode participating in curing and an electrode not participating in curing, respectively. In the boosted pulse generating means 2, the oscillating circuit 21 oscillates pulses upon receipt of the power supply from the small-sized power source 1, and the boosting circuit 22, likewise upon receipt of the power supply from the small-sized power source 1, boosts the amplitude value of the oscillated pulses (see FIG. 2A) several times and outputs them to the output end a. These boosted pulses, e.g., pulses having a pulse width of 1 μsec and a frequency of 2.5 kHz, are input to the accumulating means 3 and accumulated therein. The waveform at the output end b of the accumulating means 3 is shown in FIG. 2B. In the low frequency pulse outputting means 4, the switch control circuit 41 compares the voltage appearing at the output end b with the predetermined potential $V_{ref}$, and outputs a control signal to the switch 42 when the former exceeds the latter. Thus, the switch 42 is turned ON and the accumulated charges in the accumulating means 3 are discharged. When the constant potential is reached, the switch control circuit 41 stops outputting the control signal, resulting in an OFF state of the switch 42, and the low frequency pulse outputting means 4 outputs the low frequency pulses, e.g., pulses having a pulse width of 0.3 msec and a frequency of 5 Hz, to the output end c, as shown in FIG. 2C. These low frequency pulses are applied via the electrode K to the organism tissue. In this regard, preferably polarization charges generated in the organism tissue are discharged through the de-polarization means 5, and in this case, the waveform appearing at the output end d is shown in FIG. 2D.

Further, the pulse width and frequency of the pulses oscillated by the boosted pulse generating means 2 can be suitably selected according to the output frequency and pulse width of the switch control circuit 41 provided at the succeeding stage; 1 kHz to several hundreds kHz being normally selected.

Next, each of the constituent elements will be described in detail.

(a) Small-sized Power Source

The small-sized power source illustrated in the present example comprises a single or a plurality of button-type batteries, sheet-type batteries, coin-type batteries, cylinder-type batteries, pin-type batteries and the like. Although the configuration of the small-sized power source is not particularly restricted, a small-sized, thin-type and light-weight battery is preferable. Also, chargeable secondary batteries and the like can be used.

Figure 3A:
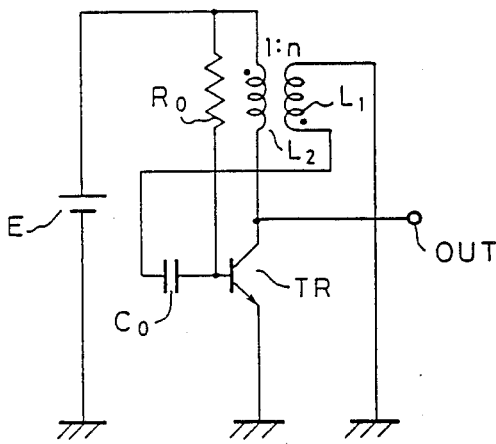
FIGS. 3A and 3B are circuit diagrams showing an example of the constitution of the boosted pulse generating means shown in FIG. 1.
Figure 3B:
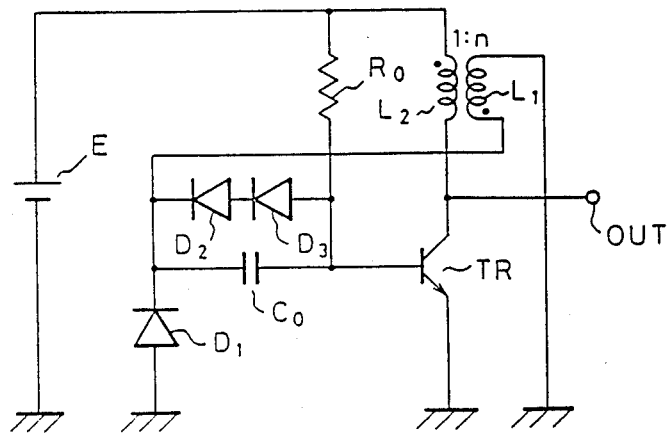

(b) Boosted Pulse Generating Means (see FIGS. 3A and 3B)

The boosted pulse generating means 2 is constituted by a combination of an oscillator such as an astable multivibrator and a boosting means consisting of an inductor, a transformer or a charged-pump type boosting circuit, or by an oscillator integrally having the boosting function such as shown in a blocking oscillator. For example, the self-running blocking oscillating circuit shown in FIG. 3A as an example can oscillate the boosted pulses by means of a transformer consisting of a base side coil $L_1$ and a collector side coil $L_2$, and a transistor TR. First, current from the power supply E through the resistor $R_0$ is supplied to the base of the transistor TR, resulting in an ON state of the transistor. Thus, current flows through the coil $L_2$ and the potential at the output terminal OUT is changed from $+E$ to 0. By the current flowing through the coil $L_2$, voltage is induced in the coil $L_1$ in the direction in which the charges of the capacitor $C_0$ are pulled out. As a result, the base potential of the transistor TR is lowered, resulting in an OFF state of the transistor, and the potential at the output terminal OUT is changed from 0 to $+E$. That is, the boosted pulses are oscillated through the switching operation of the transistor TR by the counter electro-motive force induced in the coil $L_2$. In this case, a cycle T of the oscillated pulses is represented by $T = C_0 \cdot R_0 \cdot 1_n(1+n)$. The illustration of FIG. 3A shows a most preferable example of the boosted pulse generating means capable of generating boosted pulses even though it is constituted by a small number of elements, and a modified example thereof is shown in FIG. 3B. The illustration of FIG. 3B shows as example in which the level of the base potential of the transistor TR is stabilized by adding diodes $D_1$ to $D_3$, and the usually stable boosted pulses can be oscillated regardless of a change in the voltage of the power source E.

(c) Accumulating Means and Low Frequency Pulse Outputting Means (see FIG. 4)

The accumulating means 3 and the low frequency pulse outputting means 4 define a means for accumulating the electrical energy of boosted pulses output from the boosted pulse generating means 2, and a means for outputting the accumulated charges, and the pulse width of pulses represented by the discharge charges is defined by the amount accumulated. The means 4 is constituted by the switch control circuit 41 which compares the charged amount in the accumulating means, i.e., the potential, with the predetermined threshold voltage $V_{ref}$ and outputs a signal when the former exceeds the latter, and by the switch 42 for discharging the accumulated charges in the accumulating means in response to the signal from the switch control circuit. In this case, to enable the use of a small number of circuit elements and approximate the waveform of the transduced low frequency pulse to a rectangular waveform, for example, as shown in FIG. 4, a negative resistance element N connected in parallel with the capacitor C (accumulating means) is employed. The boosted pulses input to the terminal IN from the boosted pulse generating means 2 are charged to the capacitor C and charged to the capacitor $C_1$ with the time constant $C_1 \cdot R_1$ by the capacitor $C_1$ and the resistor $R_1$. Thus, the potential at the anode terminal A of the negative resistance element N is gradually increased, and when this potential exceeds the potential at the gate terminal G, i.e., voltage $V_{ref}$ determined by the ratio of the resistors $R_2$ and $R_3$, the element N is brought to the ON state. At this time, the accumulated charges in the capacitors C and $C_1$ are discharged via the negative resistance element N and the element is brought to the OFF state at the inherent lower threshold thereof. More concretely, when the boosted pulses having a pulse width of 1 μsec, an amplitude of 24 V, and a frequency of 1 kHz to several hundreds kHz are input from the input terminal IN in FIG. 4, the capacitor C of 1 μF is charged to an extent such that the negative resistance element N is turned ON, the element N keeps the ON time at about 0.3 msec, and a single low frequency pulse having an amplitude of 24 V is output from the terminal OUT. Thereafter, by repitition of the above operation, a sequence of low frequency pulses having a frequency of 5 Hz, a pulse width of 0.3 msec, and an amplitude of 24 V are output.

Figure 8:
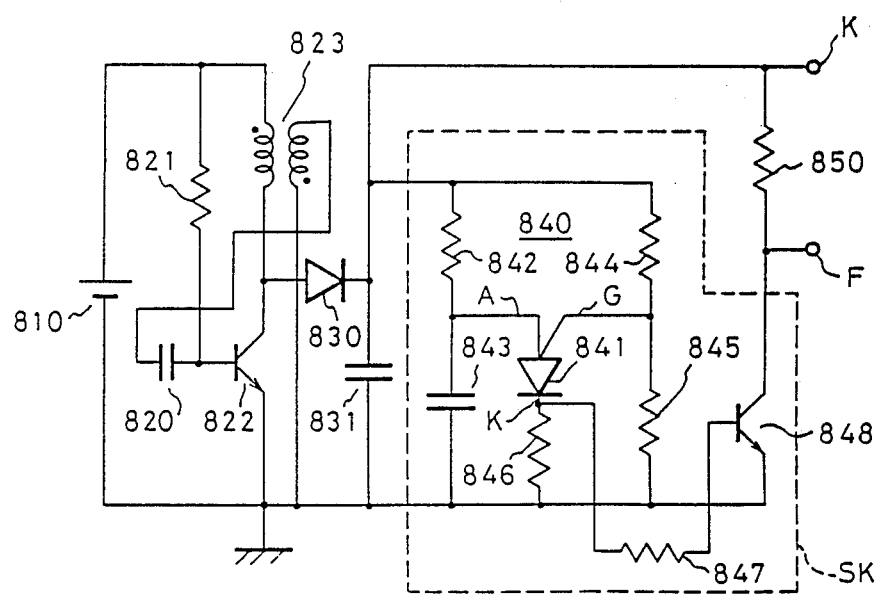
FIG. 8 is a circuit diagram showing the construction of the small-sized low frequency curing apparatus as an embodiment of the present invention.

As explained above, the combination of the negative resistance element N, the capacitors C, $C_1$, and the resistors R, $R_1$ constitutes a relaxation oscillator in which the oscillated pulses having a high energy are obtained by discharging the charges mainly in the capacitor C. The negative resistance element N is a current limiting resistance element, and concretely, may be a UJJ (unijunction transistor), a SIDAC, a PUT (programmable unijunction transistor), an n-type SCR or thyristor or the like, and is not particularly restricted. Also, employing the relaxation oscillator using a negative resistance element as a switching means and applying the voltage discharged from the accumulating means directly to the electrode are most preferable forms of implementation, since periodically stable low frequency pulses can be thus generated. A concrete application is shown in FIG. 8 as stated later.

Further, the accumulated amount should be a value sufficient for generating the stimulation current and is determined by the capacity of the accumulating means. Also, the discharge starting voltage and discharge stopping voltage are determined by the inherent value of the negative resistance element N, i.e., the time constant of the relaxation oscillator constituted by the negative resistance element.

Also, a PUT is preferably employed since the turn-ON voltage thereof is determined by the resistor connected to the anode side thereof.

The accumulating means should have an accumulating function, and an accumulatable diode or inductor such as a capacitor, a varicap and the like can be employed.

(d) De-polarization Means (see FIGS. 5A to 5C, 6 and 7)

If the pulses applied to the organism have the rectangular waveform as shown, for example, in FIG. 5A, charges (polarization charges) remaining within the organism tissue are indicated by the state as shown in FIG. 5B. In this state, when the cycle of the pulses to be applied is shortened, the supply of current to the organism is blocked by the remaining charges, resulting in very little cenesthesic stimulation. Additionally, when the voltage value of the pulses to be applied is small, the polarization influence is great.

Therefore, the de-polarization means 5 are preferably provided as shown in FIG. 1. As this means, a means for short-cutting the electrodes K and F at a predetermined point of time in the OFF duration of the pulses to be applied or a resistor having a predetermined resistance value can be employed. The short-cutting means can be set so as to operate at a predetermined time during the OFF duration of the pulses. For example, by utilizing the switching operation of the transistor, the ON state can be set for a predetermined time. According to the above constitution, an output having a great amplitude as shown in FIG. 5C can be generated in response to the input as shown in FIG. 5A. Also, when employing a means using the above resistor, if the value of the resistor is set to a value by taking a skin resistance into consideration, an effective depolarization operation can be effected even under continual installation conditions. This is a preferable embodiment from the viewpoint of minimization. Regarding the value of the resistor, about 100 kΩ at maximum is suitable. Also, the OFF duration of the pulses indicates a time interval from a fall of a certain pulse to a rise of a next pulse. Preferably, the de-polarization operation is effected at a time of the fall of a pulse.

Figure 6:
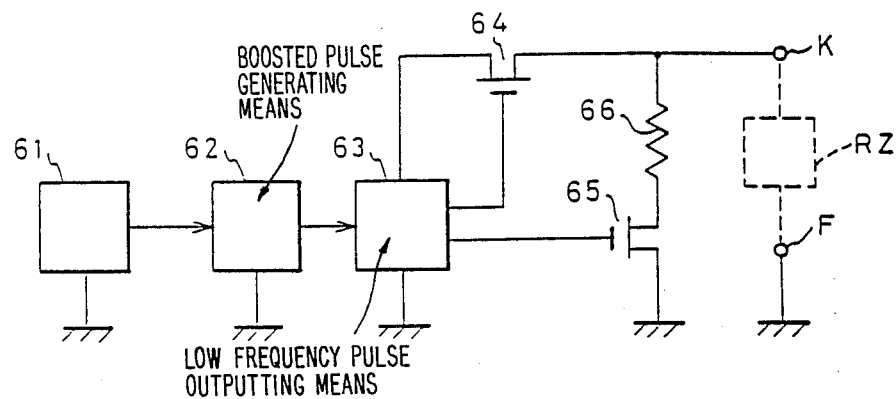
FIG. 6 is a circuit diagram showing an embodiment of the de-polarization means.
Figure 7:
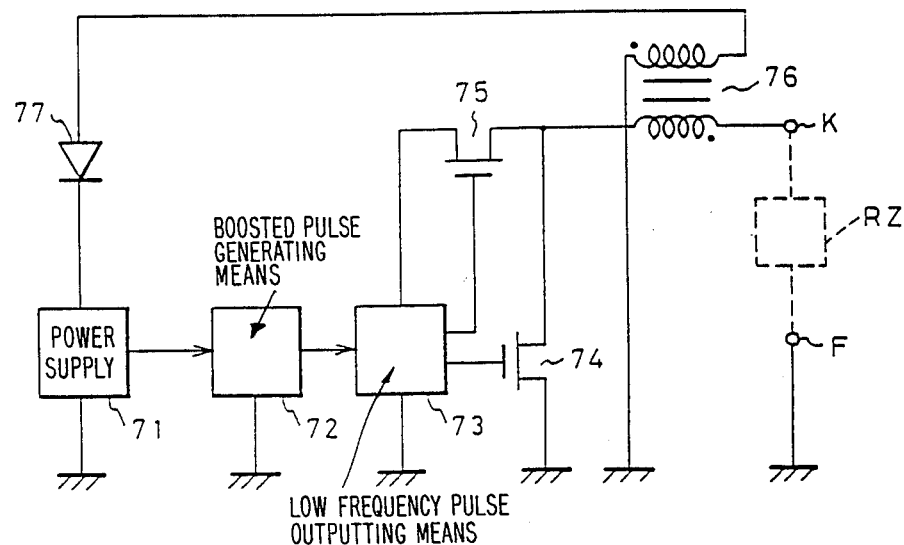
FIG. 7 is a circuit diagram showing another embodiment of the de-polarization means.

An embodiment of the de-polarization means is shown in FIG. 6, in which 61 denotes a power supply, 62 the boosted pulse generating means, and 63 the low frequency pulse outputting means including the accumulating means. 64 denotes a switching means (field effect transistor) which is turned ON when the pulse output from the low frequency pulse outputting means 63 is present, and turned OFF when it is absent. 65 denotes a switching means (field effect transistor) which is turned ON and OFF under reverse conditions to the conditions in the switching means 64. 66 is a resistor used as the de-polarization means, which is connected in series with the switching means 65. RZ shown in the broken line indicates a skin impedance. According to the constitution shown in FIG. 6, the low frequency pulses output from low frequency pulse outputting means 63 are applied via the switching means 64 and the electrode K to the load, i.e., the organism. When the pulse falls, the switching means 64 is turned OFF and the switching means 65 turned ON. Thus, the polarization charges generated by the pulses applied to the load RZ are discharged via the switching means 65. As a further embodiment of the de-polarization means, an arrangement can be employed in which the resistance body and short-circuited state is set and the polarization charges are collected in the circuit, instead of being discharged, and are used as part of the power supply voltage. In this case, it is possible to decrease the amount of power consumption and use an even longer time.

An embodiment in which the polarization charges are collected as described above is shown in FIG. 7, in which 71 denotes a power supply. The power supply 71 is a power supply for operating the apparatus of the present invention and for accumulating electrical energy generated by the collection of the polarization charges, and consists of, e.g., a secondary battery and a capacitor. 72 denotes the boosted pulse generating means and 73 denotes the low frequency pulse outputting means including the accumulating means. 74 denotes a switching means which is turned OFF when the output from the low frequency pulse outputting means 73 is present, and is turned ON when it is absent. 75 denotes a switching means which is turned ON when the output from the low frequency pulse outputting means 73 is present, and is turned OFF when it is absent. 76 denotes a transformer, the primary side of which is connected between the output of the low frequency pulse outputting means and the electrode K. Regarding the secondary side, one end is grounded and the other end is connected via a forward-direction-connected diode 77 to the power supply 71. RZ shown in the broken line denotes a load indicating a skin impedance. According to the constitution shown in FIG. 7, the low frequency pulses output from the low frequency pulse outputting means 73 are applied via the switching means 75, the primary side of the transformer 76, and the electrode K to the load. When the pulse falls, the switching means 75 is turned OFF and the switching means 74 is turned ON. Thus, the polarization charges generated by the pulses applied to the load RZ are discharged via the switching means 74. At this time, a voltage is induced in the secondary side of the transformer 76 and the current generated by the induced voltage is collected via the diode 77 at the power supply 71.

Additionally, means for collecting the polarization charges can be suitably selected by connecting another battery in parallel in the power source side, changing the turns of the transformer, or providing a voltage dropping means using resistors at a midway point, when the voltage by the polarization charges is higher than the power supply voltage.

Next, a variety of embodiments of the small-sized low frequency curing apparatus according to the present invention will be described in detail.

A circuit diagram of the small-sized low frequency curing apparatus as an embodiment of the present invention is shown in FIG. 8.

One end (+ side) of a power supply 810 using a button-type battery having a nominal voltage of 1.5 V (LR44: Matsushita Electric Industrial Co., Ltd.) is connected via the primary winding of a transformer 823 to the collector of an emitter-grounded NPN type transistor 822. Regarding the secondary winding of the transformer 823, one end is grounded and the other end is connected via a capacitor 820 to the base of the transistor 822. Also, a resistor 821 is connected between one end of the power source 810 and the base, and constitutes a self-running blocking oscillator (boosted pulse generating means) together with the constituent elements 810, 820, 822, and 823. The collector of the transistor 822, i.e., the output end of the blocking oscillator, is connected via a forward-direction-connected diode 830 to one end of a capacitor 831 and the electrode K. The other end of the capacitor 831 is grounded. Also, in parallel with the capacitor 831, a resistor 842 and a capacitor 843 connected in series with each other, and resistors 844 and 845 connected in series with each other are connected. 841 denotes a PUT (programmable unijunction transistor), an anode A of which is connected to the connection point between the resistor 842 and the capacitor 843, a gate G thereof is connected to the connection point between the resistors 844 and 845, and a cathode K thereof is grounded via a resistor 846. The constituent elements 841 to 846 constitute a relaxation oscillator 840.

The output end of the relaxation oscillator 840, i.e., the cathode K of the PUT 841, is connected via a resistor 847 to the base of an NPN type switching transistor 848. The collector of the switching transistor 848 is connected to the electrode F and the emitter thereof is grounded. A resistor 850 for effecting de-polarization is connected between the electrodes K and F. In FIG. 8, the portion shown by the broken line SK corresponds to the low frequency pulse outputting means.

Next, the operation of the small-sized low frequency curing apparatus shown in FIG. 8 will be described.

First, a DC voltage of 1.5 V from the power supply 810 is applied to the transformer 823 and input via the primary winding thereof to the collector of the transistor 822. Based on the voltage induced in the secondary side of the transformer 823 and the capacitor 820 charging or discharging via the resistor 821, the transistor 822 effects a switching operation. At this time, a counter electro-motive force generated in the transformer 823 is boosted to 25 V and input via the diode 830 to the capacitor 831. In this case, emission of the accumulated charges to the boosted pulse generating means is blocked by the inverse bias of the diode 830. When the accumulated charges in the capacitor 831 are increased, simultaneously the potential of the capacitor 843 in the relaxation oscillator 840 including the PUT 841 rises. When this potential exceeds the potential at the gate G, the PUT 841 is brought to the ON state. At this time, the charges in the capacitor 843 are discharged via the PUT 841 and input to the base of the transistor 848, resulting in an ON state of the transistor 848. As a result, the charges in the capacitor 831 are supplied via the electrode K to the load, i.e., the organism. In this case, low frequency pulses are set to a frequency of 5 Hz and a pulse width of 0.3 msec. Charges of the PUT 841 in the relaxation oscillator 840 are decreased by discharging, and when a certain amount of charges is reached, the transistor 848 is turned OFF. Thereafter, the accumulating operation of the capacitor 831 is again effected and the above-mentioned operation is repeated. In the quiescent period of the low frequency pulses, the charges polarized in the organism are discharged via the resistor 850 and the de-polarization operation is effected.

Additionally, the cycle of the low frequency pulses is determined by the charging speed determined by the resistor 842 and the capacitor 843 in the relaxation oscillator 840, and the switching operation determined by the resistor 845 and the inherent value of the PUT 841.

Also, the pulse width of the high frequency boosted pulses is determined by an inductance and a stray capacitance of the transformer 823, and the cycle thereof is determined by a product of a value of the resistor 821 and a value of the capacitor 820. However, the above is not restrictive and can be suitably selected.

As described above in detail, according to the embodiment based on the circuit constitution in FIG. 8, it is possible to realize an apparatus which consists of a very small number of circuit elements, can be used at a low power supply voltage and minimized to an extent such that it can be applied.

Additionally, although the low frequency output pulses take the form of periodically outputting rectangular pulses, they can take the form of trapezoidal waves, modified waves and the like. Also, it is possible to adapt the output pulses to a variety of cenesthesic stimulation forms by non-periodically outputting such modified waves. In this case, the amplitude, cycle and waveform of the output pulses are suitably selected.

Figure 9A:
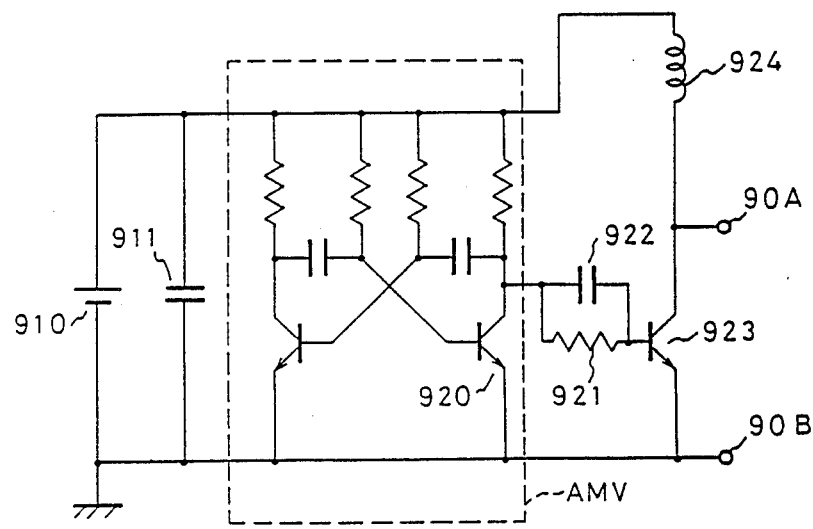
FIGS. 9A and 9B are circuit diagrams showing the construction of the small-sized low frequency curing apparatus as another embodiment of the present invention.
Figure 9B:
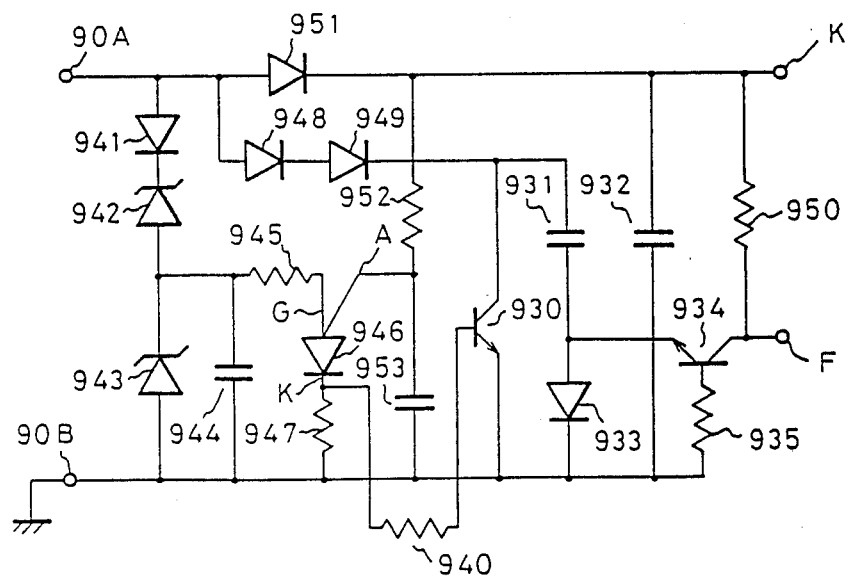

Circuit diagrams of the small-sized low frequency curing apparatus as another embodiment of the present invention are shown in FIGS. 9A and 9B. A circuit in FIG. 9A corresponds to the small-sized power source 1 and the boosted pulse generating means 2 shown in FIG. 1, and a circuit in FIG. 9B corresponds to the accumulating means 3, the low frequency pulse outputting means 4 and the de-polarization means 5 shown in FIG. 1. The embodiment shown in FIGS. 9A and 9B provides a low frequency curing apparatus capable of boosting the amplitude of the output low frequency pulses substantially up to two times or more.

First, in FIG. 9A, 910 denotes a power source using a button-type battery having a nominal voltage of 1.5 V (LR44: Matsushita Electric Industrial Co., Ltd.). In parallel with this power source 910, a capacitor 911 for stabilizing voltage and an astable multivibrator AMV (shown in the broken line) are connected. Also, one end (− side) of the power source 910 is grounded and the other end (+ side) is connected to one end of an inductor 924. The other end (terminal 90A) of the inductor 924 is connected to the collector of an NPN type transistor 923 and the emitter (terminal 90B) of the transistor is connected to one end (− side) of the power source 910. The output of the astable multivibrator AMV, i.e., the collector of the transistor 920, is connected via a resistor 921 and a capacitor 922 connected in parallel with each other to the base of the transistor 923. Output terminals 90A and 90B are connected to input terminals 90A and 90B in FIG. 9B.

In FIG. 9B, a forward-direction-connected diode 941 and two backward-direction-connected Zener diodes 942, 943 are connected in series between the terminals 90A and 90B. A capacitor 944 is connected in parallel with the Zener diode 943, one end of the capacitor 944 is connected via a resistor 945 to the gate G of the PUT 946, and the other end of the capacitor 944 is connected via a resistor 947 to the cathode K of the PUT 946. The terminal 90A is connected via two forward-direction-connected diodes 948 and 949 to the collector of an NPN type transistor 930 and one end of a capacitor 931. The other end of the capacitor 931 is connected via a forward-direction-connected diode 933 to the terminal 90B, the emitter of the transistor 930 is connected to the terminal 90B, and the base thereof is connected via a resistor 940 to the cathode K of the PUT 946. Also, the terminal 90A is connected via a forward-direction-connected diode 951 to a resistor 952, a capacitor 932 and the electrode K. The resistor 952 is connected to the anode A of the PUT 946 and connected via a capacitor 953 to the terminal 90B. The other end of the capacitor 932 is also connected to the terminal 90B. Also, the emitter of an NPN type transistor 934 is connected to the anode side of the diode 933, the collector of the transistor is connected to the electrode F, and the base thereof is connected via a resistor 935 to the terminal 90B. A resistor 950 as the de-polarization means is connected in parallel between the electrodes K and F.

The voltage supplied by the power source portion constituted by the power source 910 and the capacitor 911 having a large capacity and connected in parallel with the power source is applied to the astable multivibrator AMV and the inductor 924. The ON and OFF operation of the transistor 920 constituting part of the astable multivibrator AMV generates high frequency pulses, which turn the switching transistor 923 ON and OFF. On the other hand, the boosting inductor 924 accumulates charges in the OFF state of the transistor 923, and emits current in the ON state of the transistor 923. By the counter electro-motive force generated through the ON and OFF operation of the transistor 923, the supply voltage is boosted several times and output at the terminal 90A.

Additionally, regarding the astable multivibrator AMV, the value of each element is selected so that the oscillating frequency is about 1 kHz to 100 kHz.

Also, the capacitor 922 is connected in parallel with the resistor 921 so as to increase the speed of the switching operation of the transistor 923.

Next, the operation of the present embodiment of the apparatus will be described with reference to FIG. 9B.

The voltage input from the terminal 90A indicates boosted pulses output at the output end 90A in FIG. 9A, the voltage of which is made constant by the Zener diode 942 and supplied to the resistor 945. In this case, the Zener diode 943 shapes the amplitude of the boosted pulses, and the capacitor 944 makes the voltage of the pulses constant and decreases the change in the voltage supplied to the resistor 945. Also, the boosted pulses are supplied via the diode 951 to the resistor 952 and the capacitor 953, and to the capacitor 932. On the other hand, the boosted pulses are supplied via two diodes 948 and 949 to the capacitor 931 and accumulated therein. When the potential of the capacitor 953 gradually rises and the anode potential exceeds the gate potential given through the resistor 945, the PUT 946 is brought to the ON state. Thus, charges of the capacitor 953 flow through the PUT 946. When the charges are supplied via the resistor 940 to the base of the switching transistor 930, this transistor 930 is turned ON. The accumulated charges in the capacitor 931 are discharged via the switching transistor 930 and supplied via the resistor 935 to the base of the switching transistor 934. Thus, the switching transistor 934 is brought to the ON state and the capacitor 932 starts to discharge. Therefore, the capacitors 932 and 931 are brought to the series-connection state through the switching transistor 930 in the ON state. As a result, the charges of the capacitor 931 and those of the capacitor 932 are added, and the low frequency pulse voltage is applied via the electrode K to the organism. In this case, the voltage to be applied is substantially twice that of the embodiment in FIG. 8, since the series-connection state is realized. Since the switching transistor 934 is in the ON state, a closed circuit including a skin resistance is formed and the currents flow based on the dual voltages applied via the electrode K to the skin.

The generation of low frequency pulses is carried out by the ON and OFF operation of the switching transistor 934, the cycle thereof is determined by an inherent value of the PUT 946 and a resistance value of the resistor 945, and the frequency thereof is suitably selected to be 1 Hz to several hundreds Hz.

On the other hand, when the switching transistor 934 is in the OFF state, a de-polarization operation is effected since the polarization charges generated by the low frequency pulse voltage applied to the skin in the ON state of the switching transistor 934 are discharged via the resistor 950. Also, two series-connected diodes 948 and 949 are provided for preventing the boosting inductor 924 from being destroyed by the discharging operation of the capacitor 931 based on the switching operation of the switching transistor 930 and preventing the overcurrent flow into the boosting inductor 924 in the ON state of the switching transistor 930.

Figure 10:
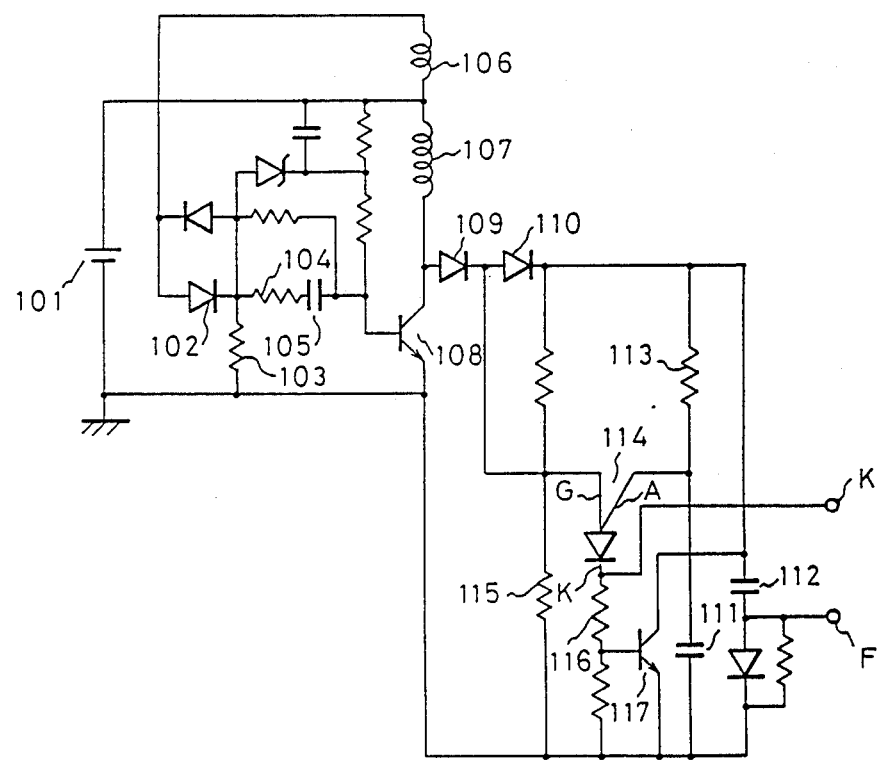
FIG. 10 is a circuit diagram showing the construction of a modified example of the embodiment shown in FIGS. 9A and 9B.

A circuit diagram of a modified example of the small-sized low frequency curing apparatus shown in FIGS. 9A and 9B is shown in FIG. 10. The feature of this circuit is that the charges accumulated in a capacitor 111 participating in the ON and OFF operation of a PUT 114 are utilized as energy of the low frequency output pulse. Regarding the constitution form of the boosted pulse generating means, the fundamental constitution is the same as that of the above-mentioned embodiments, although there is a minor difference. Thus, only the operation thereof will be described.

First, when the current from a power supply 101 is supplied to the base of a transistor 108, the transistor 108 is turned ON, resulting in a current flow through an inductor 107. The induced current by the inductor 107 flows through an inductor 106. By this induced current, a capacitor 105 is charged via a diode 102 and a resistor 104 so that the base side of the transistor 108 is at a negative level. As a result, the transistor 108 is turned OFF and then the charges accumulated in the capacitor 105 are discharged via the resistors 104 and 103. Thus, the base potential of the transistor 108 is inverted from negative to positive, and the transistor 108 is turned ON again. Therefore, boosted pulses generated through the ON and OFF operation appear at the collector of the transistor 108 and are charged via diodes 109 and 110 to capacitors 111 and 112, respectively. In this case, the capacitor 111 is gradually charged because it is charged via a resistor 113. The terminal voltage of the capacitor 111 is supplied as the anode voltage of the PUT 114. This anode voltage is compared with the gate voltage set by a resistor 115, and when the former exceeds the latter, the PUT 114 is turned ON. When the PUT 114 is turned ON, the charges of the capacitor 111 are discharged via the PUT, output at the terminal K, and supplied via a resistor 116 to the base of a transistor 117. Thus, the transistor 117 is turned ON.

In this case, when the organism impedance is connected between the terminals K and F, the discharging current from the capacitor 111 flows through the PUT 114, terminal K, organism, terminal F, capacitor 112, and transistor 117 into the capacitor 111, i.e., in the form of a loop. At this time, since the capacitor 112 is discharged in a like manner, the energy of the capacitor to be substantially applied to the organism is the sum of the energy of the capacitor 111 and that of the capacitor 112. After the discharge of the capacitors 111 and 112, the anode voltage is decreased, resulting in an OFF state of the PUT 114. While the PUT 114 is in the OFF state, the polarization charges generated within the organism are discharged via the resistor 116 and the de-polarization operation is effected.

In each of the above-mentioned embodiments, an arrangement using a PUT as a switching element in the low frequency pulse outputting means is described. However, the PUT is an element effecting the ON and OFF operation based on the relationship of the magnitude between the anode potential and the gate potential, and this gate potential may be influenced by the change in the power source voltage, as is obvious from the aforementioned circuit arrangements. To solve this problem, several circuit arrangements proposed by the present applicant will be hereinafter described in detail.

Figure 11:
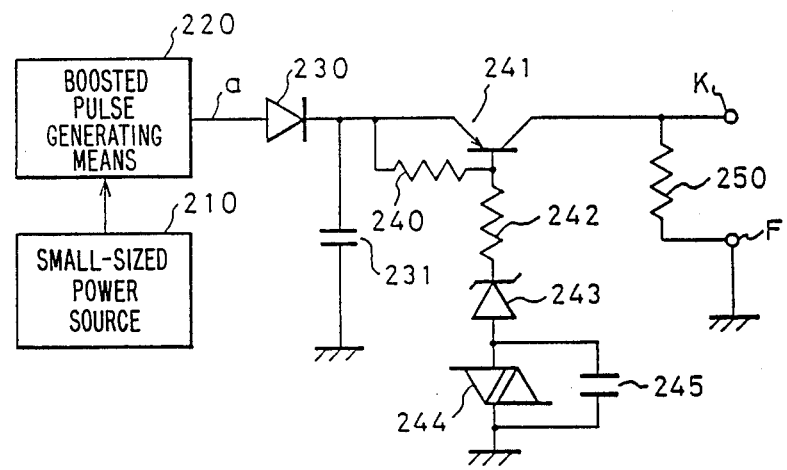
FIG. 11 is a circuit diagram showing the construction of the small-sized low frequency curing apparatus as still another embodiment of the present invention.

A circuit diagram of the small-sized low frequency curing apparatus as still another embodiment of the present invention is shown in FIG. 11.

Figure 12:
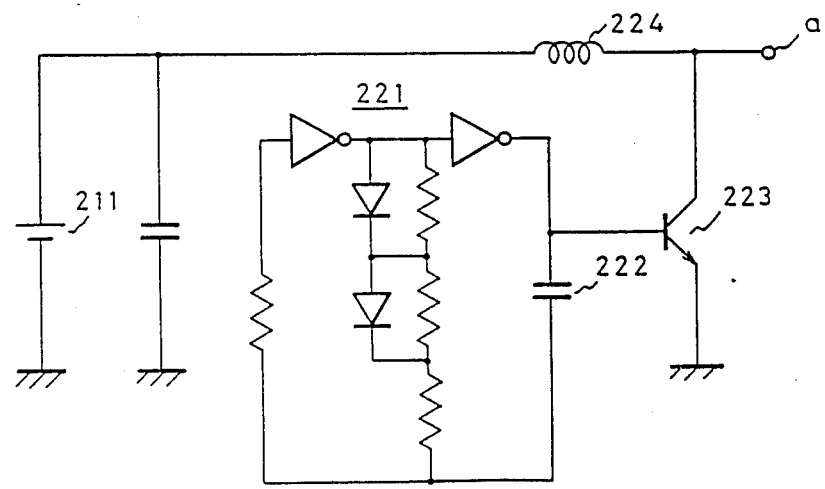
FIG. 12 is a circuit diagram showing an example of the construction of the small-sized power source and boosted pulse generating means shown in FIG. 11.

In FIG. 11, 210 denotes a small-sized power source and 220 denotes the boosted pulse generating means, a concrete arrangement of which is shown in FIG. 12. In FIG. 11, the output of the boosted pulse generating means 220 is connected to the anode of a diode 230, and the cathode of the diode is connected to a capacitor 231, a resistor 240, and the emitter of a transistor 241, respectively. The capacitor 231 is a means for accumulating the output of the boosted pulse generating means 220. The transistor 241 is used as a switch and, in this case, a PNP type transistor is used. The other end of the resistor 240 is connected via the base of the transistor 241 and a resistor 242 to the cathode of a Zener diode 243. The anode of this Zener diode 243 is connected to a triggering diode 244 (hereinafter referred to as a diac (DIC) 244) and a capacitor 245. The DIC 244 and the capacitor 245 are connected in parallel. The collector of the transistor 241 is connected to the output end (electrode K). The DIC 244 is turned ON by the occurrence of a breakdown in the predetermined terminal-to-terminal voltage. Additionally, the operation of the above DIC can be realized by substituting an element such as an SRD, an SSS and the like. Thus, the element is not restricted to a DIC. A resistor 250 as the de-polarization means is connected between the electrodes K and F.

Next, the operation of the apparatus in FIG. 11 will be described using FIG. 12.

First, electrical energy from a micro battery 211 such as a button-type battery in the small-sized power source 210 is input to an oscillating circuit 221. This oscillating circuit 221 constitutes an astable multivibrator and generates rectangular wave pulses having a higher frequency than the stimulation pulses. The rectangular wave pulses are input to a transistor 223, resulting in an ON and OFF of the current flowing through an inductor 224. Thus, a counter electro-motive force is generated in the inductor 224, i.e., the boosted pulses obtained by boosting the energy of the micro battery 211 are output at the output end a. This output end a in FIG. 12 corresponds to a node a shown in FIG. 11, and the boosted pulses are accumulated via the diode 230 at the capacitor 231.

At this time, the terminal voltage of the capacitor 231 gradually rises and the capacitor 245 is gradually charged via the resistors 240, 242, and the Zener diode 243. The terminal voltage of the DIC 244 is gradually increased by the charging in the capacitor 245, and when the voltage reaches the breakdown voltage, the DIC 244 is turned ON resulting in a quick discharge of the charges accumulated in the capacitor 245. At the same time, since the base potential of the transistor 241 is decreased, resulting in a voltage difference between the base and the emitter, the transistor 241 is turned ON and, accordingly, the energy accumulated in the capacitor 231 is output at the output end K.

On the other hand, since the capacitor 245 is discharged and its terminal voltage decreased, resulting in a decrease in the currents flowing through the DIC 244, the DIC 244 is turned OFF. Also, since the capacitor 231 is discharged and the emitter potential of the transistor 241 is decreased, the transistor 241 is brought to the OFF state. Thereafter, energy is accumulated again in the capacitor 231 and the capacitor 245. When the transistor 241 is in the OFF state, the polarization charges accumulated in the organism are discharged via the resistor 250 and the de-polarization operation is effected.

By repeating the above process, the low frequency stimulation pulses are generated. The pulse width thereof is determined by the resistors 240, 242, the capacitor 245, and the magnitude of the organism impedance.

The intensity of the low frequency output pulses in the embodiment in FIG. 11 depends upon the capacitance of the capacitor 231 and the accumulation potential. For example, an embodiment where the capacitance of the capacitor 231 is limited, or where the voltage of boosted pulses from the boosted pulse generating means is not sufficient, will be described with reference to FIG. 13.

Figure 13:
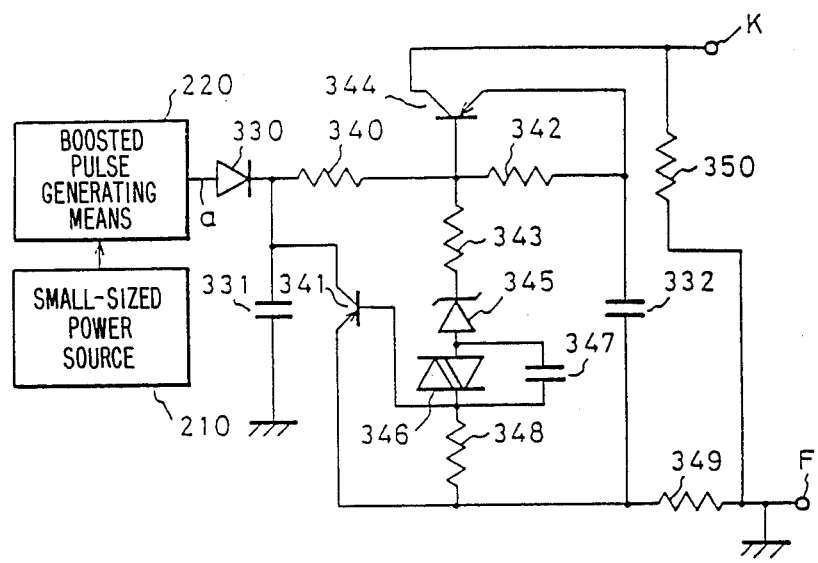
FIG. 13 is a circuit diagram showing the construction of a modified example of the embodiment shown in FIG. 11.

The illustrating of FIG. 13 indicates the embodiment shown in FIGS. 9A and 9B, i.e., the low frequency curing apparatus capable of boosting the amplitude of the low frequency pulses by two times or more.

In FIG. 13, the small-sized power source 210 and the boosted pulse generating means 220 have the same constitution as those in FIG. 11.

The output of the boosted pulse generating means 220 is connected to the anode of a diode 330 and the cathode of the diode 330 is connected to a capacitor 331, a resistor 340, and the collector of a transistor 341. The other end of the resistor 340 is connected to resistors 342, 343 and the base of a transistor 344, and the collector of the transistor 344 is connected to the output end K. The other end of the resistor 343 is connected to the cathode of a Zener diode 345, and the anode of the Zener diode 345 is connected to a DIC 346 and a capacitor 347. The DIC 346 and the other end of the capacitor 347 are connected to a resistor 348 and the base of the transistor 341, and the other end of the resistor 348 is connected to the emitter of the transistor 341, a resistor 349, and a capacitor 332. The other end of the resistor 349 is connected to the output end F. The other end of the capacitor 332 is connected to the resistor 342 and the emitter of the transistor 344. Also, a resistor 350 as the de-polarization means is connected between the output ends K and F.

The operation of the embodiment in FIG. 13 based on the above circuit constitution will be described.

The boosted output pulses from the boosted pulse generating means 220 are input via the diode 330 to the capacitor 331. At this time, the transistors 341 and 344 are in the OFF state. At the same time, the capacitor 332 is charged via the resistors 340 and 342, and the capacitor 347 is charged via the resistor 343 and the Zener diode 345. Thus, the terminal voltage of the DIC 346 gradually rises, and when the voltage reaches the breakdown voltage, the DIC 346 is turned ON and the current flows to the direction of the resistor 348, resulting in an ON state of the transistors 341 and 344. In this state, the capacitors 331 and 332 are connected in series via the transistor 341, and thus a doubled voltage is generated and output via the transistor 344 to the output end K. Additionally, the transistor 344 is constituted by a PNP type, but may be constituted by an NPN type. Also, the ratings of the capacitors 331, 332, and other electrical elements are not restricted and can be suitably selected. Moreover, for the transistors, it is devious that any active element having switching characteristics can be used.

Figure 14:
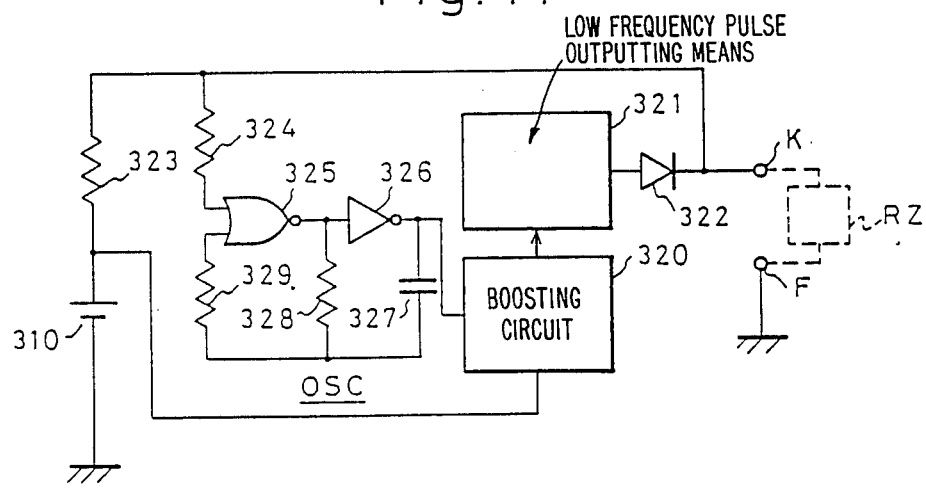
FIG. 14 is a diagram showing a modified example of the embodiment shown in FIG. 11, illustrating an example of the constitution of the circuit when about to operate upon the wearer.

Furthermore, a preferable embodiment in concrete use, i.e., an example of the constitution of the circuit at a start of operation upon the wearer, is shown in FIG. 14.

In FIG. 14, a boosting circuit 320 consists of the inductor 224 and the switching element 223 shown in FIG. 12, and low frequency pulse outputting means 321 can have the circuit constitution shown in FIG. 11 or FIG. 13. The output of the outputting means 321 is connected via a diode 322 to the output end K and via a resistor 323 to a battery source 310. The resistor 323 has a much greater value of resistance than the organism impedance, and the end opposite to the power source 310 of the resistor is connected to a resistor 324. The other end of the resistor 324 is connected to one input of a NOR gate 325. The NOR gate 325 and an inverter 326 constitute an astable multivibrator OSC together with a capacitor 327 and resistors 328, 329. The output of this astable multivibrator OSC is connected to the boosting circuit 320.

Next, the operation of the small-sized low frequency curing apparatus based on the constitution in FIG. 14 will be described.

Initially, assuming that there is nothing connected between the output ends K and F and that, at this time, one input of the NOR gate 325 is supplied with the output of the small-sized power source 310 via the resistors 323 and 324, and is at the "high" level. In this case, the oscillating circuit OSC does not effect an oscillating operation since the output of the NOR gate 325 is at the "low" level irrespective of the level of the other input of the NOR gate 325. Note, when the organism impedance RZ is connected between the output ends K and F, a majority of connects from the small-sized power source 310 flow into the organism impedance RZ. That is, since one input of the NOR gate 325 becomes "low" level, the oscillating circuit OSC starts an oscillating operation. In this case, the resistor 323 and the organism impedance RZ are selected under the condition of (323) >>(RZ). Additionally, although the above oscillating circuit OSC is constituted by utilizing gates, it is not restricted to that constitution since any oscillating circuit in which an oscillating operation is stopped by the change in the load impedance upon the wearer can be employed.

Figure 15:
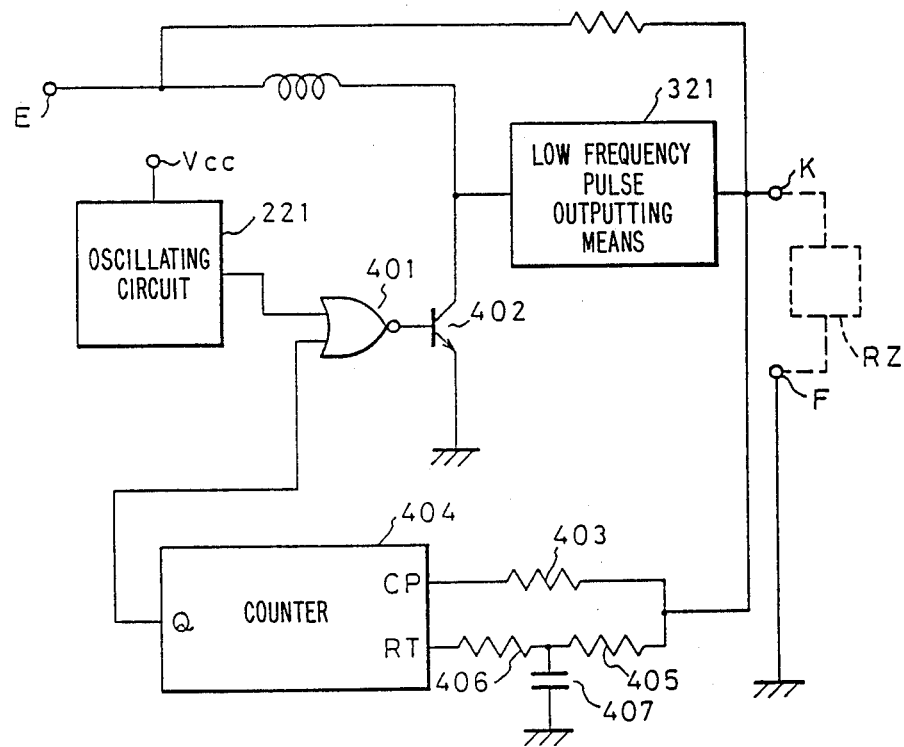
FIG. 15 is a diagram showing a modified example of the embodiment shown in FIG. 11, illustrating an example of the constitution of the circuit automatically stopping the operation after start of the operation.

Furthermore, an example of the circuit constitution of the small-sized low frequency curing apparatus automatically stopping operation after start of the operation is shown in FIG. 15.

In FIG. 15, 221 denotes the oscillating circuit 221 shown in FIG. 12, and 321 denotes the low frequency pulse outputting means shown in FIG. 11, FIG. 13, or FIG. 14. The output signal from the oscillating circuit 221 is input to one input of a NOR gate 401, and the output of the NOR gate 401 is input to the base of a transistor 402. The output of the low frequency pulse outputting means 321 is output as the low frequency pulses at the output end K, is input via a resistor 403 to the clock input end CP of a counter 404, and is input via resistors 405 and 406 to the reset input end RT of the counter 404. In this case, the reset input end RT is at the "high" level when the organism impedance RZ is not connected between the output ends K and F and the counter 404 is in the reset state. Also, when the organism impedance RZ is connected, the low frequency pulses are input via the resistor 403 to the input end CP. At this time, at the reset input end RT, the low frequency pulses are integrated by the resistor 405 and the capacitor 407 and become "low" level. Thus, the counter 404 is brought to the counting state. The counter 404 counts pulses, and when the counted value reaches a predetermined value, the output end Q changes from "low" level to "high" level. When one input of the NOR gate 401 is at the "high" level, the output thereof is at the "low" level irrespective of the state of the other input and, accordingly, the output operation stops. Therefore, when the counter 404 counts the predetermined count value, the output thereof Q is at the "high" level, and thus the NOR gate 401 is closed and the generation of low frequency pulses is cut off. Additionally, although the above counter 404 is constituted so that the counting thereof is effected based on the low frequency output pulses, it is also possible to effect the counting based on the pulses generated at the oscillating circuit 221.

Figure 16:
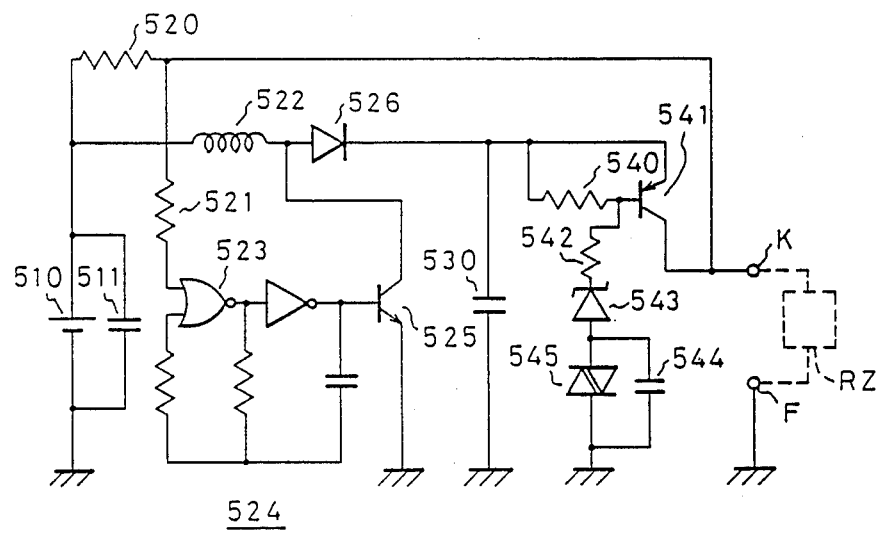
FIG. 16 is a circuit diagram showing the construction of a modified example of the embodiment shown in FIG. 14.

An overall circuit constitution of the small-sized low frequency curing apparatus using a DIC (diac) as a switching element is shown in FIG. 16.

In FIG. 16, 510 denotes a power source comprising a button-type battery having a nominal DC voltage of about 3 V (2LR53: Matsushita Electric Industrial Co., Ltd.). The output of the battery 510 is connected via a resistor 520 to the output end K and input via resistors 520 and 521 to one input of a NOR gate 523 in an astable multivibrator 524. The output of the astable multivibrator 524 constituted including the NOR gate 523 is input to the base of a switching transistor 525. This astable multivibrator 524 oscillates pulses having a frequency of about 1 to 2 kHz. The collector of the switching transistor 525 is connected to one end of an inductor 522, and the other end thereof is connected to the power source 510. Also, the collector of the switching transistor 525 is connected to the anode of a diode 526, and the cathode thereof is connected to a capacitor 530 (about 0.1 $\mu$F), a resistor 540, and the emitter of a PNP type transistor 541. The other end of the resistor 540 is connected to the base of the transistor 541 and via a resistor 542 to the cathode of a Zener diode 543. The anode of the Zener diode 543 is connected to a capacitor 544 and a DIC 545 connected in parallel with each other. The collector of the transistor 541 is connected directly to the output end K, to which the organism impedance RZ is connected via an electrode and the like. Additionally, the impedance RZ and the resistor 520 have the relationship (520)>(RZ).

Next, the operation of the low frequency curing apparatus based on the circuit constitution in FIG. 16 will be described.

First, before the impedance RZ is connected, the output of the battery 510 is input via the resistors 520 and 521 to one input of the NOR gate 523 in the astable multivibrator 524 at the "high" level. Thus, the output of the NOR gate 523 is at the "low" level irrespective of the level at the other input of the NOR gate 523. Therefore, the oscillating operation is not effected.

Next, when the impedance RZ is connected, the potential at one input of the NOR gate 523 is input via the resistor 521 to the body resistance RZ. At this time, the potential at one input of the NOR gate 523 indicates a value divided by the resistor 520 and the impedance RZ, and is at the "low" level. Thus, the NOR gate 523 is opened and the oscillating operation is started. The battery energy is intermittently supplied to the inductor 522 by the output signal of the astable multivibrator 524, and thus the counter electro-motive force is generated in the inductor 522. For example, the peak value of this counter e.m.f. is about 50 V, and the pulses to the diode 526 are the boosted pulses having a frequency of 1 to 2 kHz and a peak amplitude of 50 V. The boosted pulses are input to the capacitor 530. Since the transistor 541 is initially in the "OFF" state, the boosted pulses are accumulated in the capacitor 530. At the same time, the boosted pulses are charged via the Zener diode 543 to the capacitor 544, and thus the terminal voltage across the capacitor 544 gradually rises. When the terminal voltage of the capacitor 544 reaches a predetermined value, the DIC 545 becomes "ON" and the capacitor 544 starts to discharge, resulting in an "ON" state of the transistor 541. The electrical energy accumulated in the capacitor 530 is applied via the transistor 541 to the organism impedance RZ.

By the discharge of the capacitor 544, the terminal voltage of the DIC 545 is gradually decreased and quickly turned "OFF". Thus, the transistor 541 is turned OFF and the discharge of the capacitor 544 quickly ceases.

Figure 17:
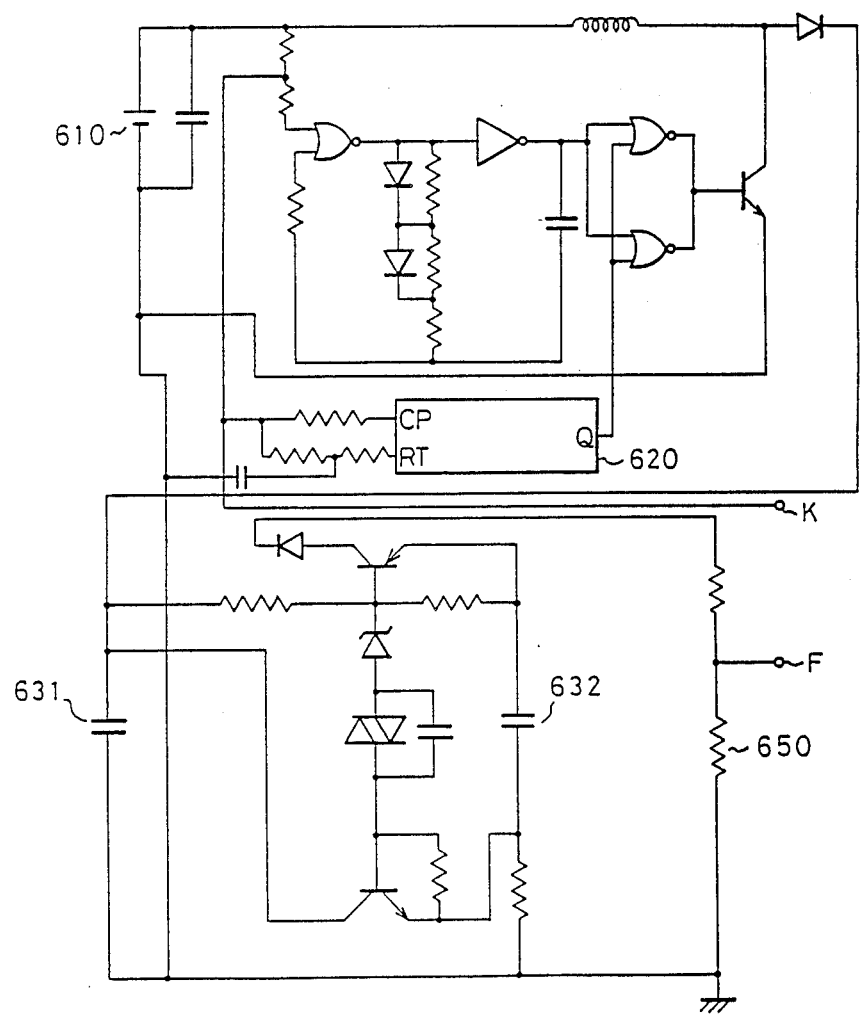
FIG. 17 is a diagram showing a modified example of the embodiment shown in FIG. 11, illustrating an example of the constitution of the circuit about to start to operate upon the wearer and automatically stopping the operation after the start of the operation.

Furthermore, an example of the constitution of the circuit starting to operate upon the wearer of the small-sized low frequency curing apparatus on the organism and automatically stopping the operation after a predetermined time is shown in FIG. 17.

The circuit shown in FIG. 17 is a combination of means capable of boosting the amplitude of low frequency pulses up to twice or more that shown in FIG. 13 (capacitors 631 and 632 in FIG. 17), the boosted pulse generating means shown in FIG. 15, means starting to operate upon the wearer shown in FIG. 14, means automatically stopping the operation after a predetermined time shown in FIG. 15, and a resistor 650 as the de-polarization means. Since the constitution and operation are as aforementioned, the explanation will be omitted. The power source 610 employs a micro battery (a button-type battery having a nominal voltage of 3 V) and can generate cenesthesic low frequency pulses. Here, an additional operation is unnecessary during use, and a continuous use of over 100 hours can be realized since the dissipation of energy is restrained as much as possible. Moreover, the present apparatus is very simple and can be made small in size by the integration thereof.

As described above by way of several embodiments, the present invention realizes the low frequency curing apparatus capable of generating low frequency pulses having a predetermined voltage and current by generating boosted pulses in the small-sized power source such as a small-sized battery, accumulating the boosted pulses in, for example, a capacitor, and discharging the accumulated charges instantly. Also, the apparatus according to the present invention has a simple constitution, and thus gives remarkable effects in practice, e.g., it can be made smaller in size to an extent such that it can be applied to the skin.

Also, it is possible to produce sufficient electrical energy to stimulate the organism from a power source having a small absolute capacity, and thus to generate stable low frequency stimulation pulses. Furthermore, the low frequency curing apparatus according to the present invention not only possesses the form suitable for reduction to an extent such as a bandage, but also can realize a long-time and stable operation.

The overall construction of the small-sized low frequency curing apparatus of the present invention will be hereinafter described with reference to several embodiments.

Figure 18A:
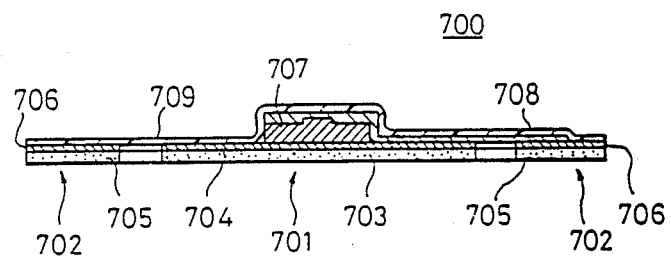
FIGS. 18A and 18B are diagrams showing an example of the overall construction of the small-sized low frequency curing apparatus of the present invention.
Figure 18B:
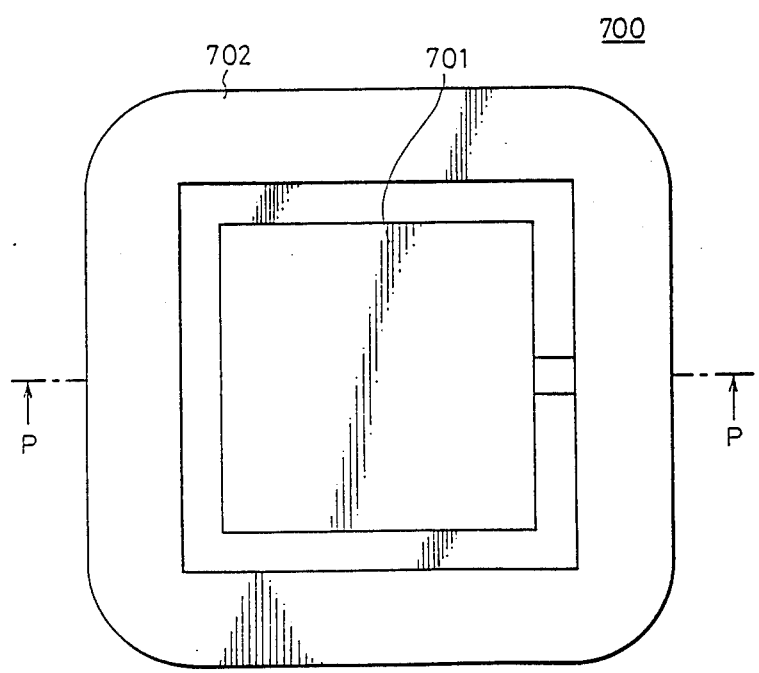

FIGS. 18A and 18B illustrate an example of the overall construction. FIG. 18A is a cross sectional view taken along the line P—P in FIG. 18B. In the figures, 700 denotes a small-sized low frequency curing apparatus constructed as the type which can be applied to the skin, i.e., the plaster type, and comprises an electrode 701 participating in curing and an electrode 702 not participating in curing. The electrode 701 is integrally formed by laminating a skin-adhesive conductive gel layer 703 formed into a flexible sheet or film and a conductive material layer 704 formed by a metal foil such as an aluminium foil, conductive rubber, resin film, carbon film, conductive paint or the like. Also, the electrode 702 is integrally formed by laminating a skin-adhesive conductive gel layer 705 formed into a flexible sheet or film and a conductive material layer 706 formed by the above aluminium foil or the like. A power source unit 707 is mounted approximately in the center of the upper surface of the electrode 701. This power source unit 707 is provided to include a hybrid circuit having a power source, e.g., a button-type battery and the de-polarization means, and to contact one output terminal thereof, e.g., the minus terminal, with the conductive material layer 704. Also, the plus terminal of this power source unit 707 is connected to the conductive material layer 706 of the electrode 702 through a lead line 708 of, for example, aluminium foil, the lower surface of which is coated with insulating material except the vicinity of the side ends of the unit. 709 denotes an insulating backing layer, which consists of, for example, non-conductive synthetic resins formed into a flexible sheet or film. The electrode 701 and the electrode 702 are arranged apart from each other on the insulating backing layer 709 and stuck to the layer.

Next, the operation and use of the small-sized low frequency curing apparatus constructed as described above will be described. First, the apparatus is applied to the position requiring the curing on the body, so that the electrode 701 is in contact with that position. At this time, the electrode 701 and the electrode 702 constitute a closed circuit, and thus the constitution in which pulses can be oscillated in realized. As a result, the low frequency pulses can be applied via the electrode 701 to the body.

According to the present example, it is possible to obtain the small-sized low frequency curing apparatus which can be applied directly to the body skin, easily operated, light-weight and can provide sufficient curing effects.

Figure 19A:
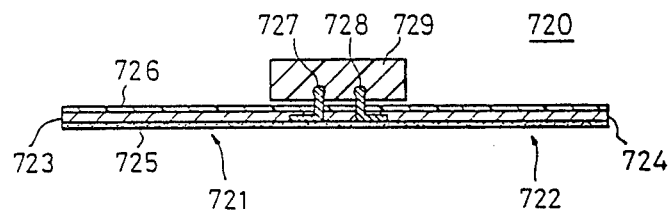
FIGS. 19A and 19B are diagrams showing another example of the overall construction; and, FIG. 20 is a diagram showing still another example of the overall construction.
Figure 19B:
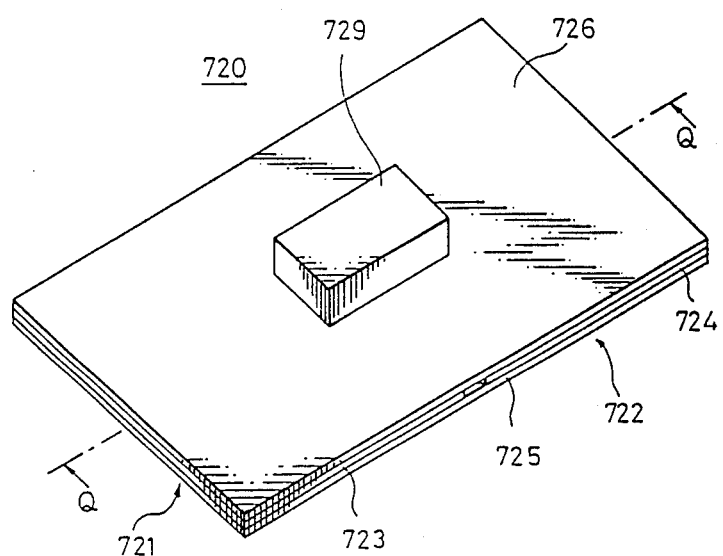

Another example of the overall construction is shown in FIGS. 19A and 19B. FIG. 19A is a cross sectional view taken along the line Q—Q in FIG. 19B. In the figure, 720 denotes a small-sized low frequency curing apparatus, 721 denotes an electrode participating in curing, and 722 denotes an electrode not participating in curing. The conductive material layers 723 and 724 of the electrodes 721 and 722, respectively, are arranged at a space of about 5 mm. A conductive gel layer 725 thinly formed into a thickness of about 0.3 mm is applied so as to cover the whole of the lower surface of the conductive material layers. Also, the electrodes 721 and 722 are integrally supported and coupled by an insulating backing layer 726. 727 and 728 are terminals connected to the electrodes 721 and 722, respectively. The top portions of the terminals 727 and 728 penetrate through the insulating backing layer 726 and project therefrom. A power source unit 729 including a small-sized power source and an electronic circuit is electrically connected and mechanically supported by the terminals 727 and 728.

The use of the small-sized low frequency curing apparatus of the present example is the same as in the aforementioned first embodiment, and thus the explanation will be omitted. According to the present example, the conductive gel layer to be arranged on the electrodes 721 and 722 is constructed by applying a single conductive gel layer 725 to the conductive material layers 723 and 724, and thus a small leak current flows between the electrodes. However, since the conductive gel layer per se possesses a resistance and the distance between the conductive material layers 723 and 724 is much greater than the thickness of the conductive gel layer 725, the resistor body arranged between the electrodes 721 and 722 can function as the de-polarization means.

According to the form shown in FIGS. 19A and 19B, it is possible to obtain the effects of a very simple and efficient manufacturing process, besides the effects in the aforementioned first embodiment. That is, it is possible to obtain a device by mounting only terminals and a power source on a portion cut off with a predetermined length from a tape-like sheet which is constructed by laminating a conductive gel layer, a conductive material layer, and an insulating backing layer. This is very useful from the viewpoint of mass production. Furthermore, by shortening the arrangement distance of both terminals and mounting a power source approximately in the center of the upper surface of the device, it is possible to substantially disregard the influence of the size of the power source on the whole device. Thus, even if the device is applied to a curved surface on the body, it is possible to use the device without losing flexibility.

Figure 20:
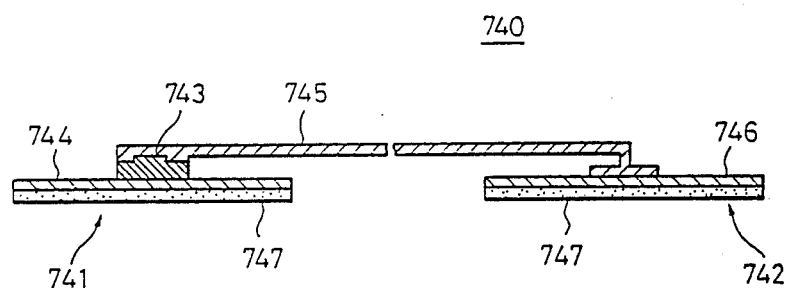

Still another example of the overall construction is shown in FIG. 20. In the figure, 740 denotes a device representing a small-sized low frequency curing apparatus, 741 denotes an electrode participating in curing, and 742 denotes an electrode not participating in curing. 743 denotes a power source unit, the minus terminal of which is connected to a conductive material layer 744 of the electrode 741, and the plus terminal of which is connected via a lead line 745 to a conductive material layer 746 of the electrode 742. 747 denotes a conductive gel layer.

According to the present example, since the electrode 741 and the electrode 742 can be applied to the body with a suitably spaced distance within the length of the lead line 745, it is possible to use the device even when the region on which it is to be applied is small or has a relatively great curvature. Also, even if the skin sweats greatly during use in hot and humid conditions, the electrodes are not influenced by the current flowing through the epidermis since they are spaced apart, and thus a good skin-adhesive low frequency curing apparatus of a plastic type can be obtained.

The skin-adhesive conductive gel is an electrically conductive gel having good skin-adhesive properties, and it is preferable to use a gel of the type disclosed in Japanese Unexamined Patent Publication No. 54-77489 which corresponds to U.S. Pat. No. 4,125,110 issued Nov. 14, 1978.

We claim:

1. A small-sized low frequency curing apparatus comprising:
    a small-sized low voltage and direct-current power source;
    a boosted pulse generating means for generating a train of boosted pulses at a high frequency upon receipt of electrical energy from said power source;

an electrical energy accumulating means operatively connected to said boosted pulse generating means, for accumulating electrical energy of said train of pulses generated from said boosted pulse generating means during a predetermined time period defined to accumulate said electrical energy at least to a stimulation level sufficient for curing an object to be electrically stimulated;

a low frequency pulse outputting means operatively connected to said electrical energy accumulating means, for outputting electrical energy accumulated in said accumulating means as low frequency pulses, each defining an output time period, for use in said curing, said low frequency pulse outputting means being operated periodically and alternately together with said accumulating means; and a pair of electrodes provided on a sheet-like member having a skin-adhesive electrically conductive layer and operatively connected to said low frequency pulse outputting means, for transmitting said low frequency pulses from said low frequency pulse outputting means via said skin-adhesive, electrically conductive layer to said object when said pair of electrodes are applied to said object;

said power source, boosted pulse generating means, electrical accumulating means and low frequency pulse outputting means being formed integrally with at least one of said electrodes.

2. A small-sized low frequency curing apparatus as set forth in claim 1, further comprising de-polarization means operatively connected to said pair of electrodes, for discharging polarization charges which remain within said object to be stimulated after said low frequency pulses are applied to said object to be stimulated.

3. A small-sized low frequency curing apparatus as set forth in claim 2, in which said de-polarization means comprises a resistor connected in parallel with output ends of said low frequency pulse outputting means.

4. A small-sized low frequency curing apparatus as set forth in claim 2, in which said de-polarization means comprises a transformer, the primary winding thereof being connected in series with output end of said low frequency pulse outputting means, the secondary winding thereof being connected in series with said small-sized power source.

5. A small-sized low frequency curing apparatus as set forth in claim 2, in which said low frequency pulse outputting means comprises a unidirectional switching element having a control terminal and a capacitor connected in parallel with said switching element, said switching element being turned ON when a first voltage appearing across said capacitor exceeds a second voltage appearing at said control terminal according to the output of said boosted pulse generating means and turned OFF when said first voltage is below said second voltage, whereby electrical energy accumulated in said accumulating means is transduced according to ON/OFF operation of said switching element into low frequency pulses having an amplitude sufficient for said curing.

6. A small-sized low frequency curing apparatus as set forth in claim 2, in which said low frequency pulse outputting means comprises a bidirectional switching element and a capacitor connected in parallel with said switching element, said switching element being turned ON when a third voltage appearing across said capacitor exceeds a predetermined value and turned OFF when said third voltage is below said predetermined value, whereby electrical energy accumulated in said accumulating means is transduced according to ON/OFF operation of said switching element into low frequency pulse having an amplitude sufficient for said curing 7. A small-sized low frequency curing apparatus as set forth in claim 2, wherein said accumulating means comprises a plurality of capacitors, and said low frequency pulse outputting means simultaneously outputs electrical energy accumulated in said plurality of capacitors when outputting electrical energy to be transduced into low frequency pulses.

8. A small-sized low frequency curing apparatus as set forth in claim 7, further comprising operation stopping means for counting pulses generated from said low frequency pulse outputting means or said boosted pulse generating means, and stopping the generation of pulses from said boosted pulse generating means when said counted value of pulses exceeds a predetermined value.

9. A small-sized low frequency curing apparatus as set forth in claim 8, in which said boosted pulse generating means comprises a resistor for inputting current from said small-sized power source, and the output end of said low frequency pulse outputting means is connected such that current from said small-sized power source can flow thereinto, the resistance value of said inputting resistor being selected at least depending upon the magnitude of the impedance of the object to be stimulated, whereby said boosted pulse generating means starts the generation of pulses when said low frequency curing apparatus is applied via said output end to said object.

10. A small-sized low frequency curing apparatus as set forth in claim 1, in which said low frequency pulse outputting means comprises a unidirectional switching element having a control terminal and a capacitor connected in parallel with said switching element, said switching element being turned ON when a first voltage appearing across said capacitor exceeds a second voltage appearing at said control terminal according to the output of said boosted pulse generating means and turned OFF when said first voltage is below said second voltage, whereby electrical energy accumulated in said accumulating means is transduced according to ON/OFF operation of said switching element into low frequency pulses having an amplitude sufficient for said curing.

11. A small-sized low frequency curing apparatus as set forth in claim 1, in which said low frequency pulse outputting means comprises a bidirectional switching element and a capacitor connected in parallel with said switching element, said switching element being turned ON when a third voltage appearing across said capacitor exceeds a predetermined value and turned OFF when said third voltage is below said predetermined value, whereby electrical energy accumulated in said accumulating means is transduced according to ON/OFF operation of said switching element into low frequency pulses having an amplitude sufficient for said curing.

12. A small-sized low frequency curing apparatus as set forth in claim 1, wherein said accumulating means comprises a plurality of capacitors, and said low frequency pulse outputting means simultaneously outputs electrical energy accumulated in said plurality of capacitors when outputting electrical energy to be transduced into low frequency pulses.

13. A small-sized low frequency curing apparatus as set forth in claim 12, further comprising operation stopping means for counting pulses generated from said low frequency pulse outputting means or said boosted pulse generating means, and stopping the generation of pulses from said boost pulse generating means when said counted value of pulses exceeds a predetermined value.

14. A small-sized low frequency curing apparatus as set forth in claim 13, in which said boosted pulse generating means comprises a resistor for inputting current from said small-sized power source, and the output end of said low frequency pulse outputting means is connected such that current from said small-sized power source can flow thereinto, the resistance value of said inputting resistor being selected at least depending upon the magnitude of the impedance of the object to be stimulated, whereby said boosted pulse generating means starts the generation of pulses when said low frequency curing apparatus is applied via said output end to said object.

15. A small-sized low frequency curing apparatus as set forth in claim 1, wherein said small-sized low frequency curing apparatus is of the plaster-type, said electrodes each comprising an electrically conductive material layer having a skin-adhesive conductive gel layer laminated on a first surface thereof, and said power source being provided on a second surface of said conductive material layer opposite said first surface.

16. A small-sized low frequency curing apparatus as set forth in claim 1, wherein each of said pair of electrodes are provided on a single sheet-like member.

17. A small-sized low frequency curing apparatus as set forth in claim 1, wherein each of said pair of electrodes is provided on one of two separate sheet-like members connected to each other by a lead line.

* * * * *